US010709427B2

(12) United States Patent
Markoff et al.

(10) Patent No.: US 10,709,427 B2
(45) Date of Patent: Jul. 14, 2020

(54) SYSTEMS AND METHODS FOR RECONFIGURING AN ULTRASOUND DEVICE

(71) Applicant: General Electric Company, Schenectady, NY (US)

(72) Inventors: Nickolas Markoff, Naples, FL (US); Christopher M. Cone, Golden, CO (US)

(73) Assignee: General Electric Company, Schenectady, NY (US)

( * ) Notice: Subject to any disclaimer, the term of this patent is extended or adjusted under 35 U.S.C. 154(b) by 144 days.

(21) Appl. No.: 15/842,200

(22) Filed: Dec. 14, 2017

(65) Prior Publication Data

US 2018/0103933 A1    Apr. 19, 2018

Related U.S. Application Data

(60) Continuation of application No. 15/221,355, filed on Jul. 27, 2016, now Pat. No. 9,872,670, which is a
(Continued)

(51) Int. Cl.
*A61B 8/00* (2006.01)
*G01R 27/26* (2006.01)
(Continued)

(52) U.S. Cl.
CPC ............. *A61B 8/58* (2013.01); *A61B 6/583* (2013.01); *A61B 6/585* (2013.01); *A61B 6/586* (2013.01);
(Continued)

(58) Field of Classification Search
CPC ...... A61B 8/58; A61B 8/4444; G01R 31/026; G01R 31/11
See application file for complete search history.

(56) References Cited

U.S. PATENT DOCUMENTS 3,608,352 A    9/1971  Walton et al.
4,545,251 A   10/1985  Uchida et al.
(Continued)

OTHER PUBLICATIONS

United States Patent and Trademark Office, "Notice of Allowance", issued in connection with U.S. Appl. No. 13/430,261, dated Apr. 27, 2016, 18 pages.
(Continued)

*Primary Examiner* — Amy He
(74) *Attorney, Agent, or Firm* — Hanley, Flight & Zimmerman, LLC

(57) ABSTRACT

Systems and methods (the "utility") presented herein provide for the assessment of acousto-electrical probes, such as their connections (e.g., transducer leads) and their response characteristics. For example, the utility may provide for readily evaluating transducer leads that have been broken and/or detached from transducers within an ultrasound probe. Due to the increasing complexity of ultrasound probes, identification of broken and/or detached transducer leads also becomes increasingly complex. Being able to identify such disconnected transducer leads may enable a person to repair, or "reterminate", these transducer leads leading to a potentially substantial cost savings, the least of which being incurred by avoiding total replacement of an ultrasound probe.

17 Claims, 10 Drawing Sheets

Related U.S. Application Data continuation of application No. 13/430,261, filed on Mar. 26, 2012, now Pat. No. 9,429,609, which is a division of application No. 12/062,852, filed on Apr. 4, 2008, now Pat. No. 8,143,898.

(60) Provisional application No. 60/910,555, filed on Apr. 6, 2007.

(51) Int. Cl.
*G01R 31/11* (2006.01)
*A61B 6/00* (2006.01)
*G01R 31/50* (2020.01)
*G01R 31/66* (2020.01)
*G01N 29/30* (2006.01)
*G01R 31/28* (2006.01)

(52) U.S. Cl.
CPC ........... *A61B 8/4444* (2013.01); *G01N 29/30* (2013.01); *G01R 27/2605* (2013.01); *G01R 31/11* (2013.01); *G01R 31/50* (2020.01); *G01R 31/66* (2020.01); *G01R 31/2886* (2013.01); *Y10T 29/49004* (2015.01)

(56) References Cited

U.S. PATENT DOCUMENTS

| | | |
|---|---|---|
| 5,318,027 A | 6/1994 | Fukui |
| 6,314,380 B1 | 11/2001 | Seip et al. |
| 6,920,776 B2 | 7/2005 | Gessert et al. |
| 6,928,856 B2 | 8/2005 | Gessert et al. |
| 7,007,539 B2 | 3/2006 | Gessert et al. |
| 7,028,529 B2 | 4/2006 | Gessert et al. |
| 7,059,168 B2 | 6/2006 | Hibi et al. |
| 7,077,853 B2 | 7/2006 | Kramer et al. |
| 7,155,957 B2 | 1/2007 | Gessert et al. |
| 7,278,289 B2 | 10/2007 | Gessert et al. |
| 7,533,566 B2 | 5/2009 | Tung et al. |
| 7,626,399 B2 | 12/2009 | Crocked et al. |
| 7,748,901 B2 | 7/2010 | Markoff et al. |
| 2006/0052703 A1* | 3/2006 | Kumazawa ............. A61B 8/58 600/447 |
| 2007/0096029 A1 | 5/2007 | Narasimhan et al. |
| 2007/0234807 A1 | 10/2007 | Moore et al. |
| 2008/0146943 A1 | 6/2008 | Jenkins et al. |
| 2012/0271573 A1 | 10/2012 | Markoff et al. |
| 2016/0331354 A1 | 11/2016 | Markoff et al. |

OTHER PUBLICATIONS

United States Patent and Trademark Office, "Final Office action", issued in connection with U.S. Appl. No. 13/430,261, dated Sep. 14, 2015, 12 pages.

United States Patent and Trademark Office, "Non-Final Office action", issued in connection with U.S. Appl. No. 13/430,261, dated May 22, 2015, 22 pages.

United States Patent and Trademark Office, "Restriction Requirement", issued in connection with U.S. Appl. No. 13/430,261, dated Feb. 20, 2015, 6 pages.

United States Patent and Trademark Office, "Notice of Allowance", issued in connection with U.S. Appl. No. 15/221,355, dated Jul. 27, 2016, 22 pages.

* cited by examiner

SYSTEMS AND METHODS FOR RECONFIGURING AN ULTRASOUND DEVICE

CROSS-REFERENCE TO RELATED APPLICATIONS

This patent arises from an application that claims the benefit of priority, as a continuation, to U.S. patent application Ser. No. 15/221,355, filed on Jul. 27, 2016, for "SYSTEMS AND METHODS FOR RECONFIGURING AN ULTRASOUND DEVICE", which is a continuation of U.S. patent application Ser. No. 13/430,261, filed on Mar. 26, 2012, for "ULTRASOUND DEVICE TESTING," which is a divisional of U.S. patent application Ser. No. 12/062,852, filed on Apr. 4, 2008, for "SYSTEMS AND METHODS FOR RECONFIGURING AN ULTRASOUND DEVICE", now U.S. Pat. No. 8,143,898, which claims priority of U.S. Provisional application No. 60/910,555, filed on Apr. 6, 2007, for "UNIVERSAL X-RAY TEST BED" each of which is incorporated herein by reference in their entireties and priority is claimed.

BACKGROUND

Generally, manufacturers of medical equipment, such as General Electric, Siemens, Phillips, build and service the medical equipment that they develop. These manufacturers maintain detailed specifications and circuit diagrams for the equipment such that their service technicians can perform repairs and they vigilantly protect such information in order to protect their market share. For example, by closely guarding the specifications and diagrams of the x-ray device, the manufacturer may prevent others from entering the market to service and repair their brand-name devices. And, by monopolizing the service and repair market for a particular piece of equipment, the manufacturer is able to extrude even more income from a sale thereof. Accordingly, the service and repair costs associated with that device can be quite substantial, even while the sale price of a particular x-ray device is also very substantial.

In many cases, medical devices are almost prohibitively expensive. For example, doctors and hospitals in smaller markets (e.g., small towns) are often unable to afford the costs associated with such devices. Even if it were possible for the smaller market medical service providers to afford these medical devices, the costs associated with the service and repair of the devices would likely put the devices' benefits out of economic reach.

SUMMARY

Systems and methods (the "utility") presented herein provide for the assessment of acousto-electrical probes, such as their connections (e.g., transducer leads) and their response characteristics. For example, the utility may provide for readily evaluating transducer leads that have been broken and/or detached from transducers within an ultrasound probe. Due to the increasing complexity of ultrasound probes, identification of broken and/or detached transducer leads also becomes increasingly complex. Being able to identify such disconnected transducer leads may enable a person to repair, or "reterminate", these transducer leads leading to a potentially substantial cost savings, the least of which being incurred by avoiding total replacement of an ultrasound probe.

The utility may provide a means for connecting to a variety of ultrasound probes thereby providing, in essence, a universal means for identifying broken and/or detached ultrasound transducer leads. These connecting means may be implemented in variety of fashions such as a plurality of individual connectors configured with a single piece of test equipment, wherein each connector is operable with a particular ultrasound probe. Alternatively, the piece of test equipment may be configured with a communication interface that allows for the switchable replacement of a variety of connectors, again wherein each individual connector is operable with a particular ultrasound probe. In another embodiment, the piece of test equipment may be configured with an adaptable connection interface that communicates with a variety of ultrasound probe connectors. In this regard, the piece of test equipment may employ a multiplexing scheme that allows for a processor to communicate with each connector of an ultrasound probe, and thus each transducer lead of the ultrasound probe, without regard to the ultrasound probe type.

In one embodiment, a system for determining electrical leads of an acousto-electrical probe that includes a plurality of transducers includes a coupling device that includes a plurality of connectors configured for individually coupling to the electrical leads of the acousto-electrical probe, wherein a number of connectors is greater than or equal to a number of transducers in the probe. The system also includes a processor communicatively coupled to the coupling device and a storage element configured for storing software instructions that direct the processor to generate one or more control signals, wherein the one or more control signals are provided to the coupling device for a determination by the processor of an electrical characteristic (e.g., electrical conductibility) of the electrical leads.

The connectors of the coupling device may be configured as a printed circuit board. The processor is configured for determining a number of the electrical leads that are coupled to the coupling device. The software instructions may direct the processor to determine a type of acousto-electrical probe. The software instructions may include a plurality of software modules, wherein each software module corresponds to one type of acousto-electrical probe. The software instructions may also include a report generation software module that directs the processor to indicate at least one broken electrical lead of the acousto-electrical probe.

The system may further include a display interface that displays information to a user of the system, wherein the information indicates the electrical characteristic of the electrical leads. The system may further include a detector that determines an electrical characteristic of the transducers of the acousto-electrical probe. In this regard, the detector may apply a first of the one or more control signals to a first transducer of the acousto-electrical probe to determine a capacitance of the first transducer. The first of the one or more control signals may charge a capacitance of the first transducer. The system may further include a counter that counts during charging of the capacitance of the first transducer and a comparator that compares a reference voltage to a voltage of the charged capacitance of the first transducer, wherein the comparator generates a counter control signal used for stopping the counter when the voltage of the charged capacitance passes the reference voltage. The processor may determine the capacitance based at least in part on a duration between starting and stopping the counter.

In another embodiment, a method of returning an acousto-electrical device to an operational status, wherein the acouso-electrical device has a plurality of transducers includes acquiring the acousto-electrical device from an industry segment, determining a type of the acousto-electrical device, and determining a number of electrical leads from the transducers of the acousto-electrical device. The method also includes providing a connection interface to the acousto-electrical device based on the type, wherein the connection interface has a number of connectors that is greater than or equal to the number of electrical leads of the acousto-electrical device. The method also includes generating one or more control signals, transferring the one or more control signals to the connector, determining conductivity of the electrical leads of the acousto-electrical device based on the one or more control signals, and providing a connection for at least one of the electrical leads based on the determined conductivity.

Providing a connection for the at least one of the electrical leads may include configuring a printed circuit board connection to the at least one of the electrical leads. The printed circuit board connection may be a flexible printed circuit board connection. The method may further include configuring the acousto-electrical probe with reflective module while transferring the one or more control signals to the acousto-electrical probe.

In another embodiment, a method of refurbishing an ultrasound device having a plurality of transducers includes acquiring an ultrasound probe from a first medical industry segment, wherein the ultrasound device is in at least a partially inoperable state. The method also includes coupling an adaptive test module to the ultrasound probe, determining electrical conductivity of transducer leads of the ultrasound probe. The method also includes, in response to determining the electrical conductivity of the transducer leads, determining at least one broken transducer lead of the transducer leads; and reconfiguring the at least one broken transducer lead to a conductive state to return the probe a second medical industry segment.

The first medical industry segment and a second medical industry segment may be the same, such as a hospital, a health maintenance organization, a private doctor's office, an original equipment manufacturer, and a retailer of medical equipment.

Coupling the adaptive test module to the ultrasound probe may include providing a plurality of connectors with the adaptive test module. The number of the connectors, and this regard, may be greater than or equal to a number of the transducer leads. Coupling the adaptive test module to the ultrasound probe may also include generating at least one control signal to determine a configuration of ultrasound probe coupled to the adaptive test module.

In another embodiment, a method of identifying inoperable leads of an ultrasound probe includes providing a first connection interface, receiving an ultrasound probe connection interface with the first connection interface. The method also includes generating a plurality of control signals to interrogate connectors of the ultrasound probe connection interface via the first connection interface and identifying at least one broken lead of the ultrasound probe based on a corresponding at least one of the plurality of control signals.

Providing the first connection interface includes providing a plurality of connectors with the first connection interface, wherein a number of connectors of the first connection interface is greater than or equal to a number of the connectors of the ultrasound probe connection interface. Identifying at least one broken lead of the ultrasound probe may include processing a response to the corresponding at least one of the plurality of control signals. Processing the response may include determining an Ohm value based on the response to the corresponding at least one of the plurality of control signals.

Alternatively or additionally, providing the first connection interface may include providing the first connection interface with a plurality of alternative connection interfaces. In this regard, each of the first connection interface and the plurality of alternative connection interfaces may be configured with a test tool. The method may further include multiplexing the control signals based on a type of the ultrasound probe connection interface that is received. The method may further include generating information that indicates the least one broken lead of the ultrasound probe. The method may further include displaying the information to a user, wherein the information provides a location of the at least one broken lead of the ultrasound probe within the ultrasound probe connection interface.

In another embodiment, a method of determining a capacitance capability of an electrical lead includes discharging stored capacitance of the electrical lead, applying power to the electrical lead, and, during the application of power to the electrical lead, counting clock cycles from a microprocessor. The method also includes comparing a electrical lead voltage to a reference voltage, stopping the counting of clock cycles when the electrical lead voltage passes the reference voltage, processing a number of counted clock cycles, in response to stopping the counting of clock cycles to determine a capacitance of the electrical lead. The reference voltage may be between about 3 and 6 volts. The electrical lead may be coupled to a transducer configured with an ultrasound probe.

DETAILED DESCRIPTION OF THE DRAWINGS

Figure 1:
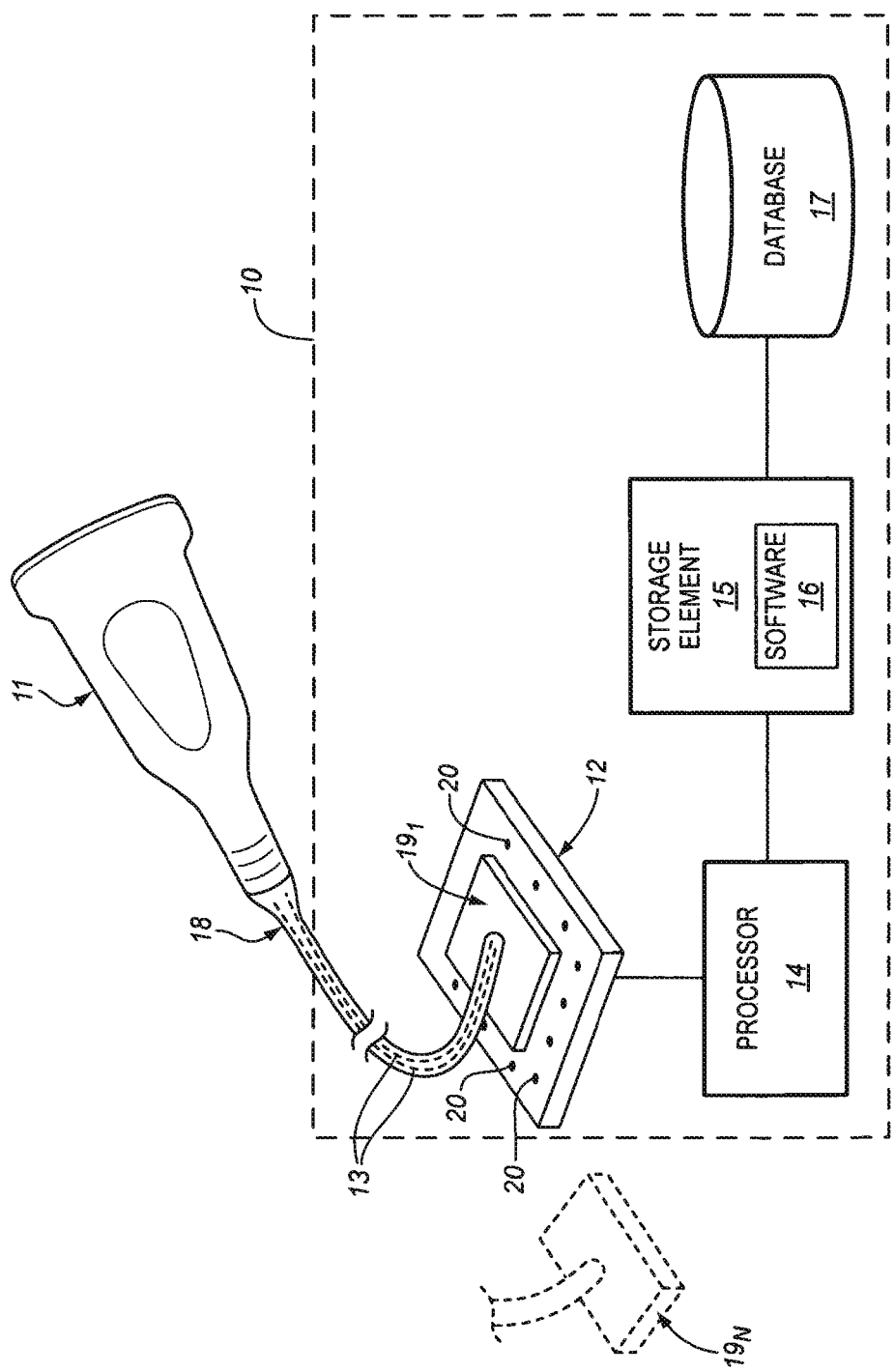
FIG. 1 is a block diagram of a system for determining decoupled leads in an acousto-electrical probe.

While the invention is susceptible to various modifications and alternative forms, specific embodiments thereof have been shown by way of example in the drawings and are herein described in detail. It should be understood, however, that it is not intended to limit the invention to the particular form disclosed, but rather, the invention is to cover all modifications, equivalents, and alternatives falling within the scope and spirit of the invention as defined by the claims.

FIG. 1 is a block diagram of a system 10 for determining decoupled leads 13 in an acousto-electrical probe 11. Often, acousto-electrical electrical probes (e.g., ultrasound probes), have leads that become detached from their respective transducers or broken due to general use and/or misuse. For example, a physician may hold an ultrasound probe under his arm when examining a patient simply because the physician requires the use of two hands when examining a patient. In this regard, the cable containing the transducer leads of the ultrasound probe (e.g., cable 18) may bend and twist in a manner that causes the transducer leads to break or detach after a period of time. Generally, however, the actually more complex and sensitive transducers of the ultrasound probe remain intact. Thus, repair of an ultrasound probe may be facilitated by repairing the broken transducer leads (e.g., reterminating the transducer leads).

Older model ultrasound probes generally had a few transducer leads. Modern ultrasound probes, however, have significantly increased the number of ultrasound leads because, among other reasons, processing capabilities have improved. For example, as processor speeds increase so do the resolution capabilities of an ultrasound device. Accordingly, ultrasound device manufacturers generally increase the number of transducers within an ultrasound probe to increase the resolution of the overall device as the processor capabilities come available. In some instances, ultrasound probes contain as many as 360 transducer leads. This dramatic increase in the number of transducer leads has led to a corresponding complexity in the repair of ultrasound probes. Accordingly, manufacturers of the ultrasound probes merely provide replacement probes at a substantial cost to the physician rather than repairing the probe.

The system 10 provides a means for analyzing the leads 13 of an acousto-electrical probe 11 that may eliminate the need for replacement probes. For example, the acousto-electrical probe 11 may assist in identifying broken and/or detached transducer leads such that a technician may repair those leads and alleviate the need for purchasing a new acousto-electrical probe. However, acousto-electrical probes are generally developed by a variety of manufacturers that adhere to no particular standard. In this regard, the acousto-electrical probes vary almost as much in the number of transducer leads 13 (shown in phantom) as they do in the different connector types. Accordingly, providing a means for identifying broken and/or detached transducer leads 13 becomes further complicated.

The system 10 may alleviate the complexity of identifying broken and/or detached transducer leads from a plurality of acousto-electrical probe types. In this regard, the system 10 may include a connection interface 12 that is configured for connecting to a plurality of acousto-electrical probe types, such as the acousto-electrical probe 11. In this regard, the connection interface 12 may provide a means for universally connecting to acousto-electrical probes of varying connection types and numbers of transducer leads.

In one embodiment, the connection interface 12 includes a plurality of connectors 20 that are configured with the connection interface 12 based on connection type information of known acousto-electrical probes. For example, the probe connection interface $19_1$ may be a connector for a certain type of ultrasound probe (e.g., brand, model, etc.) for coupling to an ultrasound device of the same brand, model, etc. The connection interface 12 may have a plurality of connectors 20 that are configured according to the probe connection interface $19_1$ of that particular brand, model, etc. However, when the system 10 is being used to test the ultrasound probe of a different brand, model, etc., the probe connection interface (e.g., the probe connection interface $19_N$, wherein N is merely intended as an integer greater than 1) may have a different number of connectors and/or a different connector configuration. In this regard, the connection interface 12 may also include connectors 20 that are configured according to known characteristics of the probe connection interface 19. An example of such a connection interface 12 is shown and described in FIG. 2.

Figure 2:
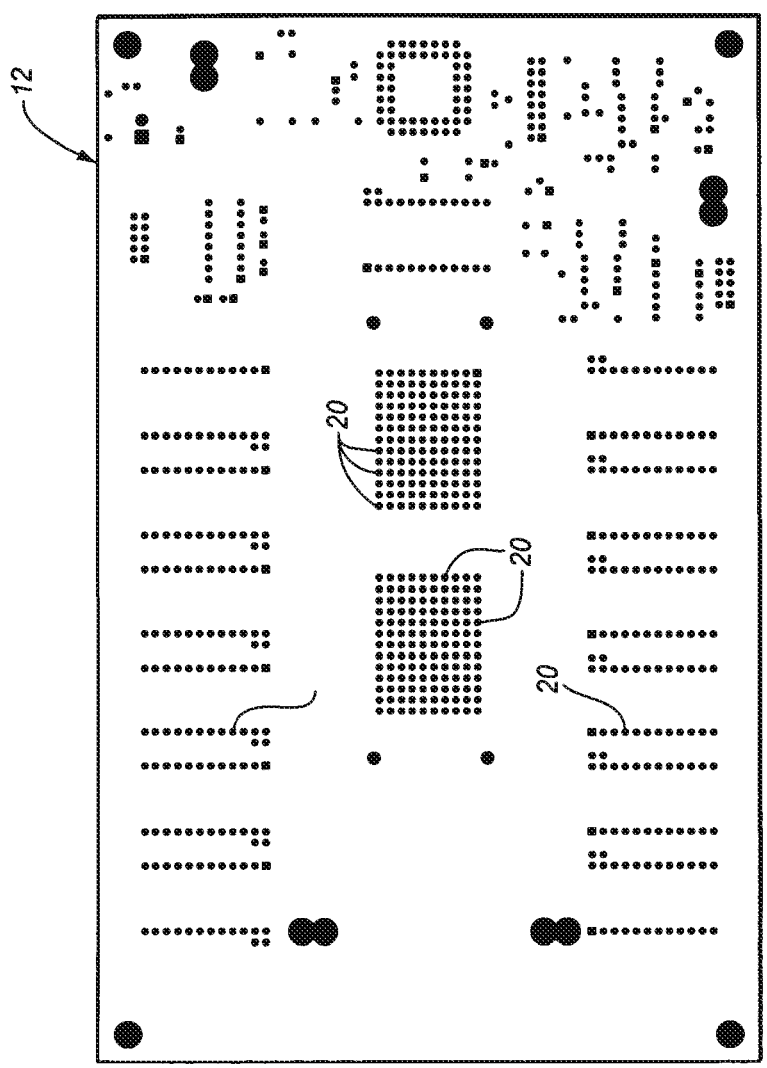
FIG. 2 is an exemplary diagram of a connector for use with a retermination test tool.

In FIG. 2, one exemplary connection interface 12 is shown in the form of a solder mask diagram. For example, known configurations of ultrasound device connectors may be ascertained from physical inspection. These configurations may then be implemented via a circuit board by generating a solder mask that has all of the connectors 20 of virtually all of the known ultrasound device types. As ultrasound probes change, and thus their respective connector configurations, the solder mask may be reconfigured as the newer ultrasound probes are introduced.

Although described with respect to implementing virtually every type of known ultrasound probe connector, the invention is not intended to be so limited. For example, a solder mask configuration may be implemented according to a desire to repair only certain types of ultrasound probes. That is, the solder mask may not include connectors 20 that are of undesirable ultrasound probes. Accordingly, the connection interface 12, and thus the solder mask of FIG. 2, may be configured as a matter of design choice, so as to form connection interfaces that are connectable to at least 2 different types of ultrasound probe connection interfaces.

Additionally, the connection interface 12 may be one that readily couples to a probe connection interface 19. For example, components of the system 10, such as the processor 14 and the storage element 15, may be configured in a single piece of test equipment. In this regard, the piece of test equipment may allow for physical switching of the connection interface 12 with other connection interfaces 12 such that the piece of test equipment can be used on a variety of acousto-electrical probes 11. Alternatively, the piece of test equipment may be configured with a variety of connection interfaces 12 that the processor 14 may communicate with to determine a type of acousto-electrical probe under test. For example, a plurality of connection interfaces 12, each of a particular ultrasound probe connector configuration, may be configured with the piece of test equipment. When an ultrasound probe is coupled to one of the connection interfaces 12, the processor 14 may determine the type of ultrasound probe based simply on the fact that the ultrasound probe is connected to a corresponding connection interface 12. In either case, the processor 14 may then perform various tests on the ultrasound probe as described herein.

Returning now to FIG. 1, once the acousto-electrical probe 11 is coupled to the connection interface 12 via its probe connection interface 19, a processor 14 may retrieve a software module 16 from the storage element 15 to determine the acousto-electrical probe 11 type (e.g., again, the brand, model, etc.) and determine whether any broken and/or detached transducer leads exist with the acousto-electrical probe 11. For example, the software module 16 may include software instructions that direct the processor 14 to interrogate the connectors 20 of the connection interface 12 to determine the number of transducer leads couple to the connection interface 12 via the probe connection interface 19. This interrogation may result in a determination of the acousto-electrical probe 11 type such that additional software instructions may be processed by the processor to determine the broken and/or detached transducer leads. For example, based on a particular configuration of the probe connection interface 19, and thus the number/configuration of transducer leads 13, a determination may be made as to the type of acousto-electrical probe. In response, the processor 14 may retrieve additional software instructions pertaining to the type of acousto-electrical probe that direct the processor to test the transducer leads 13 of the probe connection interface 19. In this regard, the software instructions may direct the processor to generate a control signal for connectors 20 that are in contact with the connectors of the probe connection interface 19. The processor 14 may then process responses to the control signals to determine whether individual transducer leads 13 are broken/detached. For example, the control signals may be used as part of an ohm metering process. In this regard, the processor 14 will determine that a transducer lead 13 is either broken or detached from its transducer when the resistance of a particular transducer lead 13 is substantially high (e.g., infinite).

Additionally, the ohm metering process performed by the processor 14 may determine electrical shorts between transducer leads. For example, although less likely, individual transducer leads generally have shielding that may deteriorate from rubbing one another over time. The individual transducer leads 13 may, therefore, come into direct contact with one another and thereby decrease the overall resistance of multiple transducer leads 13.

In one embodiment, the processor 14, as directed by the software instructions, may record certain information pertaining to the acousto-electrical probe 11 under test. For example, the processor 14 may store information regarding the transducer leads 13 that are broken and/or detached within a database 17 for future use. In this regard, a technician working on a particular acousto-electrical probe 11 may access the database and retrieve information regarding that particular acousto-electrical probe to determine which transducer leads 13 may be more susceptible to breakage and/or detachment. In other words, the processor 14 may maintain certain statistics by acousto-electrical probe 11 type.

Figure 3:
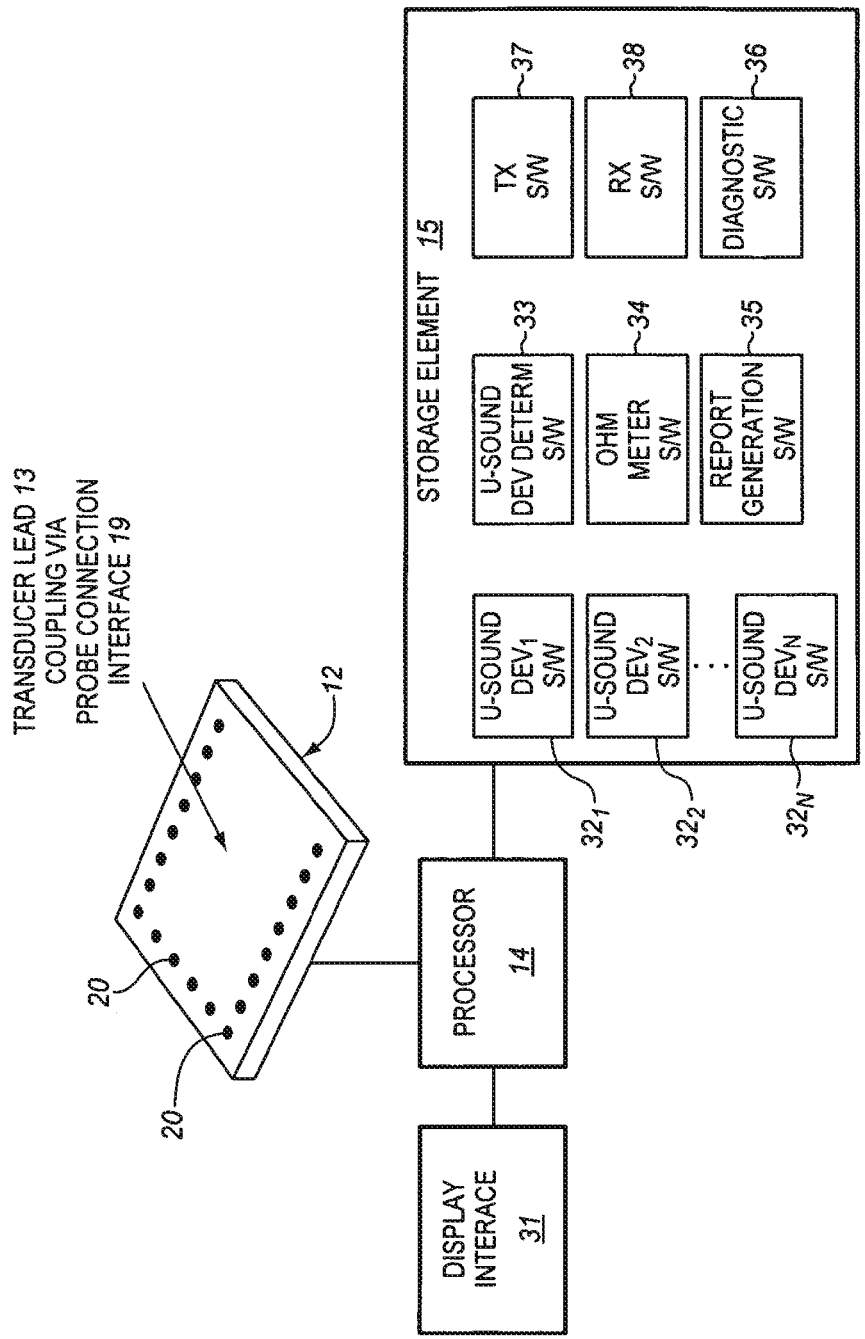
FIG. 3 is another block diagram of a system for determining decoupled leads in an acousto-electrical probe.

FIG. 3 illustrates another block diagram of the system 10 as described in FIG. 1. For example, the processor 14 is in communication with a "universal" connection interface 12 that is used for connecting probe connection interface 19 of an ultrasound probe. The processor 14 may retrieve the device determination software module 33 to initially determine the type of ultrasound probe under test (i.e., the ultrasound probe communicatively coupled to the connection interface 12). The device determination software module 33 may include software instructions that direct the processor 14 to interrogate the connection interface 12 to determine a transducer lead configuration of the probe connection interface that is coupled to the connection interface 12.

Upon interrogating the probe connection interface 19, the processor 14 may retrieve various software modules from the storage element 15 to conduct various tests on the acousto-electrical probe. These software modules may include software instructions specific to particular models of ultrasound probes. For example, the software module 32 may be used for conducting tests on a first ultrasound device type whereas the software module 32 may be used for conducting tests on a second device type. In this regard, the storage element 15 may include a plurality of software modules that are "callable" by the device specific software modules 32. For example, once a particular ultrasound probe has been determined and its appropriate software module 32 has been called, the device specific software module 32 may then call one or more of the software modules 34, 36, 37, and 38 to perform certain tests on the ultrasound probe.

One such test that may be performed on the ultrasound probe, as mentioned above, includes a broken and/or detached transducer lead test. Such may be implemented by the processor 14 when the ohm meter software module 34 directs the processor to generate control signals for the connectors 20 that are in communication with the ultrasound probe connection interface. In one embodiment, the ohm meter software module 34 and the device termination software module 33 may be implemented as a single software module. For example, the software module may be configured to direct the processor 14 to generate control signals applicable to each connector 20 of the connection interface 12. As it is unlikely that every transducer lead from an ultrasound probe is broken and/or detached, a transducer lead configuration may be determined from a portion of the overall number of transducer leads of the ultrasound probe. For example, an ultrasound probe with 192 transducers has 192 transducer leads in a particular connector configuration. If the ohm meter software module 34 determines that there are 190 transducer lead connections, the ohm software module 34 may determine that the ultrasound probe is indeed a 192 transducer ultrasound probe. Accordingly, the invention is not intended to be limited to a particular embodiment with such distinct software modules.

The storage element 15 may also include a report generation software module 35 that is used to provide the user of the system 10 with a need for quickly ascertaining various problems associated with the ultrasound probe under test. For example, the report generation software module 36 may direct the processor 14 to communicate information pertaining to broken and/or detached transducer leads to the display interface 31. The display interface 31 may be configured from a variety of information rendering devices, such as LCDs, LEDs, and/or printers. In one embodiment, the display interface may be alternatively or additionally implemented as a Personal Computer (PC) that displays the information via a computer monitor. Such information may be useful to the person using the system 10 troubleshooting the ultrasound probe under test. In one embodiment, the information is also conveyed to a database (e.g., the database 17 of FIG. 1) such that statistical information may be developed on a probe by probe basis. For example, the system 10 may compile statistical information regarding a certain type of ultrasound probe such that the processor 14 may retrieve the information from the database for display to a person using the system 10 to test a particular ultrasound probe.

In one embodiment, the software modules 37 and 38 may be used to detect the operability of the transducers themselves. For example, the transmit software module 37 may direct the processor 14 to generate a pulsed control signal that, in essence, "pings" a particular transducer such that the transducer generates an acoustic pulse (i.e., and ultrasound pulse). In this regard, the storage element 15 may also include a receive software module 38 that directs the processor to process a signal as received by the transducer. For example, a transducer may receive an acoustic pulse that is reflected from a target. The transducer may, in turn, convert the received acoustic signal into an electronic signal. The receive software module 38 may direct the processor 14 to convert the electronic signal into a digital signal (e.g., via analog-to-digital conversion, or ADC). Once in digital form, the receive software module 38 may direct the processor to call the diagnostic software module 36. In this regard, the diagnostic software module 36 may analyze the phase amplitude of the received acoustic signal via digital signal processing to determine whether a particular transducer is operating properly (e.g., operating according to certain guidelines or standards). The frequency and/or phase characterization is shown and described below in greater detail in FIGS. 11 and 12.

Although shown and described with respect to all testing software modules (e.g., the software modules 34, 36, 37, and 38) being configured within as part of a single system 10, the illustrated embodiment is merely intended as an example of how the system 10 may be configured. In other embodiments, the system 10 may be configured with fewer or more than those software modules that are shown. For example, in one embodiment, the system 10 may be configured as a field service tool that is operable to test an ultrasound device while on site. In this regard, the system 10 may not require the functionality of determining whether transducer leads are broken and/or detached, as such may require off-site repair. Accordingly, the system 10 may be configured with less functionality so as to only generally provide a certain level of "health" of the ultrasound device. Such an embodiment may include the transmit, receive, and diagnostic software (i.e., software modules 36, 37, and 38) as a means for simply determining whether the ultrasound device is operable. Moreover, even though an ultrasound probe with broken and/or detached leads may require off-site repair, a field service tool may be configured to simply diagnose the leads to determine whether the ultrasound probe requires off-site repair.

Figure 4:
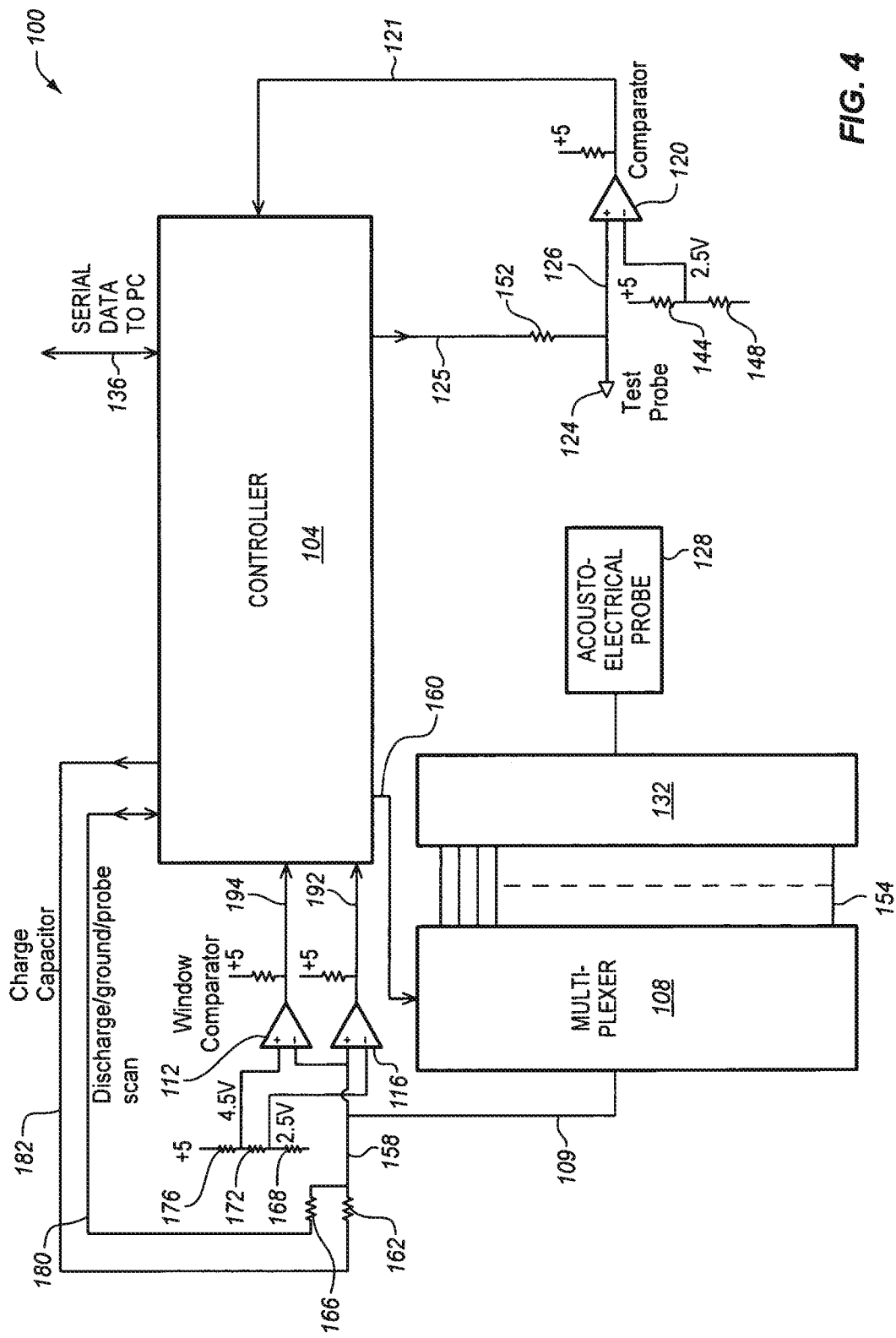
FIG. 4 is a block diagram of an exemplary retermination test tool for repairing an acousto-electrical device.

FIG. 4 is a block diagram of an exemplary retermination test tool (RTT) 100 for use by a repair operator to quickly and efficiently test an acousto-electrical probe 128. The acousto-electrical probe 128 is generally operable to emit acoustic signals and to receive echoes from those signals. In general, acousto-electrical probes generate and receive acoustic signals using a plurality of transducers located in the scan head of the probe. One type of transducer commonly used in acousto-electrical probes employs the piezoelectric effect to send and receive acoustic signals. In this type of probe, there is typically a plurality of crystals (e.g., quartz crystals) generally referred to as piezoelectric crystals positioned inside the scan head of the probe. When an electrical current is applied to the crystals, they change shape rapidly. The rapid shape changes, or vibrations, of the piezoelectric crystals produce acoustic waves that travel outward from the acousto-electrical probe. Conversely, when acoustic waves hit the crystals, they emit electrical currents. Therefore, the piezoelectric crystals may be used to send and receive acoustic waves. Generally, each of these transducers is soldered onto a printed circuit board (PCB) inside the scan head of the probe. Furthermore, a cable harness may be attached to the scan head to allow the probe to be connected to a control device such as an ultrasound machine. The cable harness usually includes a connector at the opposite end of the scan head which mates with an interface on an ultrasound machine. Inside the cable harness, the transducers are connected to the connector by a plurality of coaxial leads that are soldered to the PCB. During use in the field, the internal wiring of the acousto-electrical probe 128 can fatigue and break, typically at the PCB end, causing open circuits or short-circuits at one or more leads, which may require that the acousto-electrical probe be replaced. The RTT 100 may be used by an operator to provide notification as to which lead(s) require retermination (e.g., those leads that are broken and/or detached).

In this embodiment, the RTT 100 includes a controller 104, an analog multiplexer 108, the comparators 112, 116, 120, and a test probe 124. In the various modes of operation described below, the acousto-electrical probe 128 under test may be connected to the RTT 100 via a connector 132 of the RTT 100. Generally, the RTT 100 can be configured to mate with the connector of virtually any type of acousto-electrical probe. In this embodiment, to enable the RTT 100 to test a single lead of the acousto-electrical probe 128 at a time, the connector 132 is electrically coupled to a 1:192 channel multiplexer 108. In this regard, the output node 109 of the multiplexer 108 may be electrically coupled to a single lead of the acousto-electrical probe 128. The controller 104 may be operable to select which lead is electrically coupled to the output node 109 by controlling the multiplexer 108 via the multiplexer control lines 160. Furthermore, the output node 109 may be coupled to a test node 158, which may be used by the RTT 100 to determine various electrical characteristics of individual leads of the acousto-electrical probe 128, as described below.

The RTT 100 is now described in reference to its various modes of operation. The RTT 100 may generally have at least three general modes of operation. The first mode is Ground Scan mode, and may generally be used to identify leads that are improperly connected to ground. This can occur for various reasons, such as when the cable of the acousto-electrical probe 128 has been crushed or bent (e.g., during handling, shipping, through general use, etc.). In the Ground Scan mode, the RTT 100 may scan through the leads of the acousto-electrical probe 128 and sense whether each lead is grounded. To achieve this, the controller 104 may control the multiplexer 108 to address an input channel that corresponds to an individual lead on the acousto-electrical probe 128. As discussed above, this causes an individual lead to be electrically coupled to the test node 158, which permits the RTT 100 to sense its electrical characteristics. To determine whether the selected lead is grounded, the controller 104 may drive the discharge/ground/probe node 180 high (e.g., a logical one). If the lead addressed by the multiplexer is grounded, the test node 158 remains grounded. Conversely, if the addressed lead is not grounded, the test node 158 is pulled high through resister 166. Therefore, the voltage at the test node 158 is determinant upon whether the lead addressed by the multiplexer 108 is grounded or open.

To sense the voltage at the test node 158, the controller 104 may use the comparator 116. For example, the test node 158 may be coupled to the non-inverting input of the comparator 116 for comparison with a reference signal. The reference signal, in this embodiment, is generated by using a voltage divider (e.g., formed by the resistors 168, 172, and 176) coupled to a voltage source of 5 volts. This reference signal is input to the inverting input of the comparator 116. Furthermore, the controller 104 detects the output of the comparator via the ground scan input node 192. Those skilled in the art, however, should readily recognize that other types of voltage sensing may be used. The results of the Ground Scan may then be communicated by the controller 104 to the operator in any number of ways. For example, the controller 104 may include a serial interface 136 to communicate data to a PC. Alternatively or additionally, an exterior display such as an LCD may be coupled to the controller 104 to display information requested by the operator.

Another mode of the RTT 100, the Probe Scan mode, may be used by the operator to identify leads that are in contact with the test probe 124. This mode generally allows the operator to identify a lead under test so as to determine the location on a PCB to reterminate the lead. To achieve this functionality, the RTT 100 may include circuitry that enables it to sense when a lead addressed by the multiplexer 108 is in contact with the test probe 124. Specifically, the controller 104 may drive the test node 158 high through the resistor 166 by driving the discharge/ground/probe node 180 high. Then, the controller 104 may cause the multiplexer 108 to continuously cycle through the connector pins 154, which causes a high voltage (e.g., about 5 volts) to appear on the lead that is addressed by the multiplexer 108.

The operator may use the test probe 124 to probe various leads on the acousto-electrical probe 128. The test probe 124 may be connected to circuitry which permits the RTT 100 to determine when the test probe 124 is in contact with a node that is at a high voltage (e.g., about 5 volts), so that it may sense when the test probe 124 is in contact with the lead addressed by the multiplexer 108, as described above. In this regard, the controller 104 pulls the voltage on the test probe 124 to ground by pulling the test probe pulldown node 125 low (e.g., logical zero) through a resistor 152. When the test probe 124 is in contact with a lead of the acousto-electrical probe 128 addressed by the multiplexer 108, the voltage on the test probe 124 is driven high. Conversely, when the test probe 124 is in contact with a lead that is not addressed by the multiplexer 108, the voltage on the test probe 124 is driven low through the pulldown resistor 152.

To sense the voltage at the test probe node 126, the controller 104 may use the comparator 120. For example, the test probe node 126 may be coupled to the non-inverting input of the comparator 120 for comparison with a reference signal. The reference signal, in this embodiment, is generated by using a voltage divider (e.g., formed by the resistors 144 and 148) coupled to a voltage source of about 5 volts. This reference signal is input into the inverting input of the comparator 120. In this regard, the comparator 120 signals to the controller 104 via the test probe scan input node 121 whether the test probe 124 is at a high or ground voltage. The controller 104 may then use this information to determine which leads of the acousto-electrical probe 128 are in contact with the test probe 124. As in other operational modes, the controller 104 may communicate the information to the operator by transmitting data to an external device, such as an LCD or PC.

Another mode of the RTT 100 may be generally referred to as the Capacitance Scan mode. The Capacitance Scan mode may be used to determine the relative capacitance of each of the leads on the acousto-electrical probe 128. This mode may operate by measuring the length of time it takes to charge the capacitance of a lead to a known voltage through a high-value resistor. In this embodiment, the controller 104 first directs the multiplexer 108 to address one of the connector pins 154 that corresponds to an individual lead on the acousto-electrical probe 128. The capacitance in the lead may first be discharged to ground through a resistor 166 by having the controller 104 pull the discharge node 180 low. After the capacitance has been discharged, the discharge node 180 may then be placed into a high impedance state by the controller 104. Next, the controller 104 drives the charge node 182 high and starts an internal counter at substantially the same time. While the counter is counting, the charge node 182 charges the capacitance of the transducer lead through the high-value resistor 162.

The controller 104 may use the comparator 116 to determine when the voltage on the lead has reached a certain level (e.g., about 2.5 volts, representing a full charge of the transducer lead capacitance). In this regard, the test node 158 may be coupled to the non inverting input of the comparator 112 for comparison with a reference signal. The reference signal, in this embodiment, is generated by using a voltage divider (e.g., formed by the resistors 168, 172, and 176) coupled to a voltage source of about 5 volts. The reference signal is input into the inverting input of the comparator 116. In this embodiment, when the voltage of the lead rises to about 2.5 volts, the output of the comparator 116 is driven high. The controller 104 senses the output of the comparator 116 through the capacitance-scan input node 194. When the controller 104 detects that the comparator 116 has been "tripped", the controller 104 stops the counter.

The count from the counter can then be used by the controller 104 to determine the capacitance of a single lead of the acousto-electrical probe 128 using known relationships between capacitance, resistance, and charge times. For example, the change in time required to charge a capacitor to roughly 63 percent of full of its initial voltage may be referred to as a time constant $\tau$, which is directly proportional to the resistance and capacitance of a circuit. Practically speaking, a capacitance is fully charged after 5 time constants, or $5 \cdot \tau$. Thus, the controller may determine the capacitance of the transducer lead as follows: $C = 5 \cdot \tau \cdot R$.

Once computed, the controller 104 may then direct the multiplexer 108 to address another pin and repeat the steps described above to measure the relative capacitance of each of the leads of the acousto-electrical probe 128. As in the previously described modes of operation, the controller 104 may communicate the capacitance measurements to the operator via an external device that may include a display element.

FIGS. 5-8 together illustrate an exemplary circuit schematic of an RTT 250 that can be used to implement the RTT 100 embodiment of FIG. 4. The RTT 250 includes, in this embodiment, a 68HC11 microcontroller 200 that controls the operation of the various components of the RTT 250. The microcontroller 200 is also configured to perform data processing functions to determine multiple electrical characteristics of individual leads of an acousto-electrical probe. The 68HC11 is a CISC microcontroller family originally from Motorola, now produced by Freescale Semiconductor, that is used in many applications including barcode readers, hotel card key writers, amateur robotics, and various other embedded systems. Although other microcontrollers with similar functionality may be used, the 68HC11 microcontroller is used in this embodiment due to its memory capabilities, I/O features, and flexibility.

The specific functionality of the RTT 250 is now described in reference to certain operational modes. In Ground Scan mode, the RTT 250 may be used to determine which leads of an acousto-electrical probe are improperly grounded. In this regard, the microcontroller 200 may first drive the CHARGE node to about 5 volts. This causes the test node 300 shown in FIG. 6 to rise to about 5 volts through the resistor R500. The test node 300 may be electrically coupled to the output of a multiplexer (e.g., the multiplexer 108 shown in FIG. 4) via the RAIL_SHORT_TEST node, which may be electrically coupled to an individual lead of an acousto-electrical probe. The microcontroller 200 may then output control signals on the MUX_D0-MUX_D7 lines to direct the multiplexer to address an individual lead. The specific details of implementing and controlling the multiplexer are described below in FIG. 5.

Once an individual lead is addressed by the multiplexer, the RTT 250 may then determine whether the lead is grounded. If a lead is not grounded, the voltage at the test node 300 remains at about 5 volts due to the voltage on the CHARGE line. Conversely, if a lead is grounded, the voltage at the test node 300 is pulled to ground.

Figure 5:
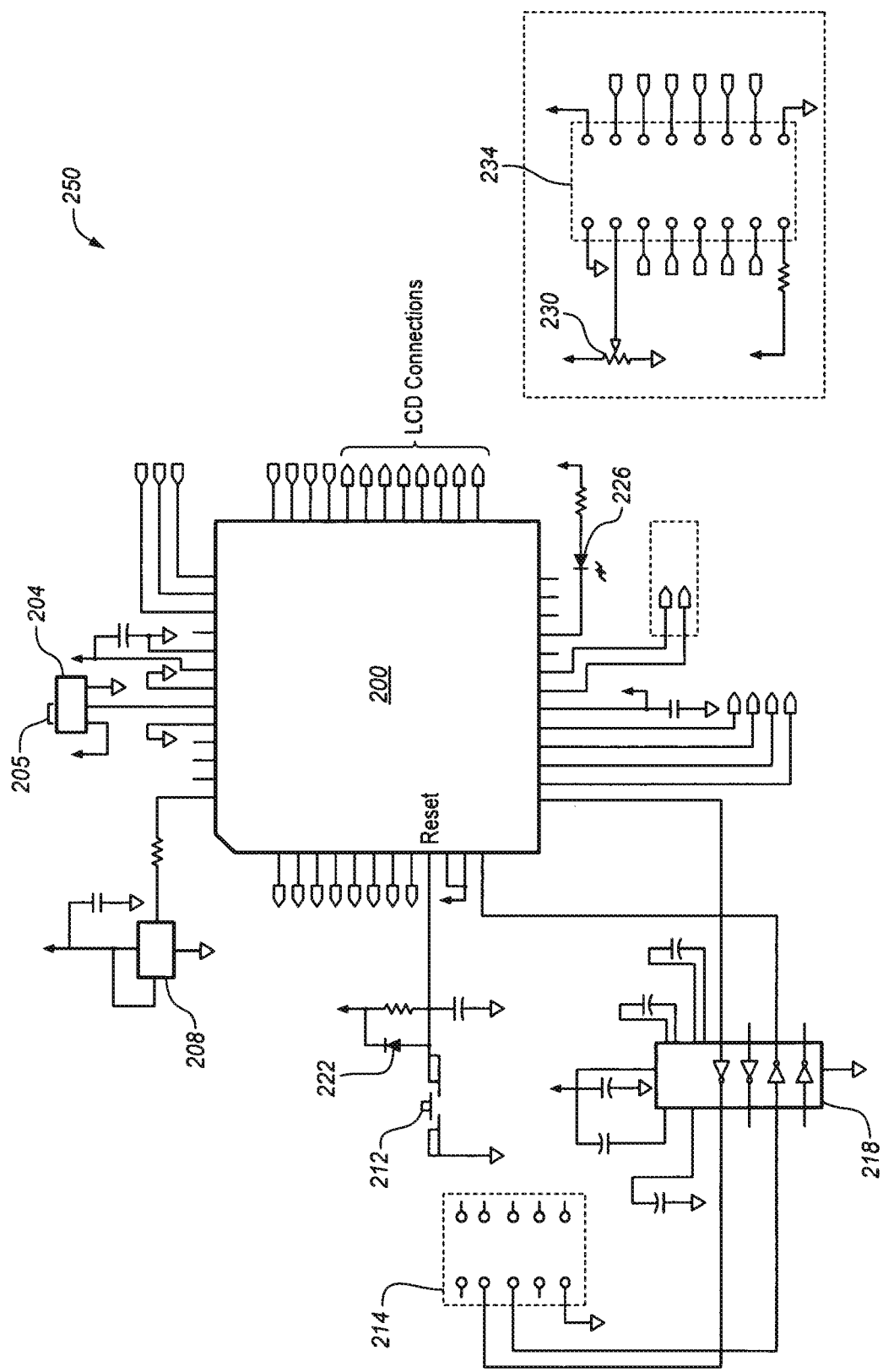
FIG. 5 is a circuit schematic of an exemplary retermination test tool for repairing an acousto-electrical device.
Figure 6:
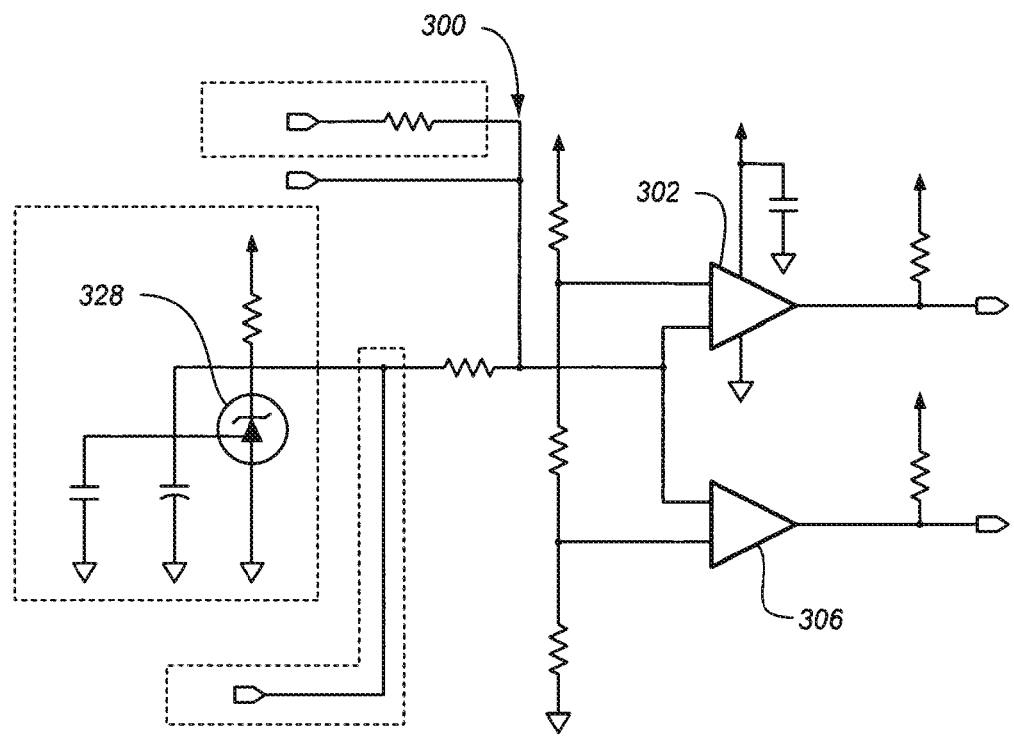
FIG. 6 is a circuit schematic of an electrical characteristic sensing module of the exemplary retermination test tool that is used to sense individual leads of transducers.

In FIG. 6, an electrical characteristic sensing module 275 senses individual leads of a transducer. In this regard, a comparator 306 of the sensing module 275 may be used to sense the voltage of an individual lead by coupling the test node 300 to its non-inverting input. A three input diode 328 is also coupled to the non-inverting input of the comparator 306 to act as a precision regulator, however, other devices, such as operational amplifiers may be used. The inverting input of the comparator 306 may be set to a reference voltage (e.g., 2.44 volts) by the voltage divider implemented using a resistor R16 (e.g., 649Ω), a resistor R17 (e.g., 2.74 kΩ), and a resistor R18 (e.g., 3.24 kΩ). The output of the comparator 306 may be electrically coupled to an input of the microcontroller 200 via the SCAN_LO line, as shown in FIG. 5. When a lead addressed by the multiplexer is grounded, the test node 300 and the non-inverting input to the comparator 306 is also grounded. Since the voltage at the non-inverting input of the comparator 306 will be lower than the voltage on the inverting input (e.g., 2.44 volts), the comparator 306 drives the SCAN_LO line to ground. This in turn may alert the microcontroller 200 that an individual lead is grounded. Conversely, when a particular lead addressed by the multiplexer is open, the test node 300 remains at about 5 volts, as previously described. In this situation, the comparator 306 may drive the SCAN_LO line high due to the voltage on the non-inverting input being greater than the voltage on the inverting input. The microcontroller 200 may then direct the multiplexer to scan through each of the individual leads to determine whether each lead is improperly grounded.

When operating in Probe Scan mode, the microcontroller 200 may drive the CHARGE node to about 5 volts which sets the voltage at the test node 300 to about 5 volts through the resistor R500. The microcontroller 200 may then direct the multiplexer to address an individual lead of an acousto-electrical probe by outputting control signals on the MUX_D0-MUX_D7 lines. As described above, this causes the lead addressed by the multiplexer to be driven to about 5 volts.

The operator may then use a test probe (e.g., the test probe 124 shown in FIG. 4), to probe various leads on an acousto-electrical probe. In this embodiment, the test probe is electrically connected to the TEST_PROBE line shown in FIG. 6. To enable the test probe to be used to sense the voltage on individual leads, the microcontroller 200 pulls the voltage on the TEST_PROBE line to ground through the COMP_PULLUP node and a resistor R4 (e.g., 10 kΩ).

Figure 7:
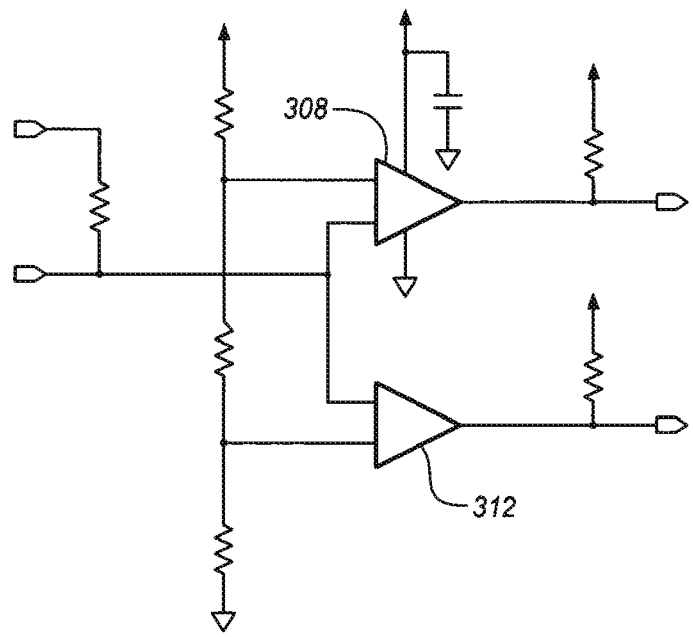
FIG. 7 is a circuit schematic of another electrical characteristic sensing module of the exemplary retermination test tool that is used to sense a test probe.

In order to determine whether the test probe is in contact with a lead addressed by the multiplexer, the comparators 308 and 312 may be used to sense the voltage on the TEST_PROBE line, as illustrated with the test probe sensing module 310 of FIG. 7. In this regard, the TEST_PROBE line may be coupled to the non-inverting input of the comparator 312, and the inverting input of the comparator 308. The inverting input of the comparator 312 and the non-inverting input of the comparator 308 may be set at a reference voltage (e.g., 2.5 volts) through the voltage divider formed by the resistors R11 and R13 (e.g., 3.24 kΩ each). The operator may then place the test probe in contact with one or more leads of the acousto-electrical probe under test. When the test probe is in contact with a lead that is not addressed by the multiplexer, the voltage on the TEST_PROBE line remains at ground due to the COMP_PULLUP line being grounded by the microcontroller 200. However when the test probe is in contact with a lead addressed by the multiplexer, the voltage on the TEST_PROBE line is about 5 volts, since the lead is electrically coupled to the test node 300, which is about 5 volts as described above. The comparators 308 and 312 sense the voltage on the TEST_PROBE line and output corresponding signals to the microcontroller 200 on the PROBE_HI and PROBE_LO lines, respectively. The microcontroller 200 may then store the data, and notify the operator which leads are in contact with the test probe.

In the Capacitance Scan mode, the microcontroller 200 may direct the multiplexer to address a pin corresponding to a lead of an acousto-electrical probe, such as the acousto-electrical probe 128 shown in FIG. 4. As in previously described operational modes, an individual lead (e.g., a lead addressed by the multiplexer) may be electrically coupled to the test node 300. Prior to starting the capacitance measurement, the microcontroller 200 may discharge the capacitance in the lead. This may be achieved by driving the DISCH_TEST node to ground, which discharges the capacitance in the lead to ground through a resistor R23 (e.g., 2.15 kΩ). The microcontroller 200 may then place the DISCH_TEST node in a high impedance state. To start the capacitance measurement, the microcontroller 200 may drive the CHARGE node to about 5 volts and start a 16-bit internal counter at substantially the same time. While the counter is counting, the voltage on the CHARGE node charges the capacitor in the lead through the resistor R500 (e.g., 2.2 MΩ). The resistance of the resistor R500 may be chosen so that the capacitance may be measured with a requisite accuracy. In this regard, if the resistance is too low, the capacitor may charge very quickly. In this case, the error in the capacitance measurement may be high because the time to charge the capacitor may not be measured accurately by the counter. For example, suppose the counter counts at a rate of one count per microsecond. If the resistance of the resistor 162 causes the capacitor to charge in 0.5 microseconds, the output of the counter may not be very useful. Problems may also arise if the resistance of the resistor 162 is too high. For example, errors may be introduced in the measurement due to leakage currents of other components. Also, if the capacitor takes too long to charge because of the high resistance value of the resistor 162, the internal counter may overflow which may result in inaccurate capacitance measurements. Moreover, a high resistance value may cause the Capacitance Scan to take an unacceptable length of time to measure the capacitance of all the leads in an acousto-electrical probe.

To sense the voltage level of capacitor, the controller 200 may use a comparator 302. The non-inverting input of the comparator 302 may be set to a reference voltage (e.g., 4.5 volts) through the voltage divider formed by the resistor R18 (e.g., 3.24 kΩ), the resistor R17 (e.g., 2.74 kΩ), and the resistor R16 (e.g., 649Ω). The inverting input of the comparator 302 may be electrically coupled to the test node 300 which corresponds to an individual lead. In operation, the output of the comparator 302 may be tripped when the capacitor voltage rises to the reference voltage. The microcontroller 200 senses the output of the comparator 302 via the SCAN_HI node, as shown in FIG. 6. When the microcontroller 200 detects that the output of the comparator 302 has been tripped, the microcontroller 200 stops the counter. Then, using known relationships between capacitance, resistance, and charge time, the count from the counter can be used to determine the capacitance of an individual lead of the acousto-electrical probe. For example, the microcontroller 200 may use an empirically derived lookup table to determine the capacitance when provided with a number from the counter that corresponds to a length of time. Alternatively, the microcontroller 200 may input the number returned from the counter into a formula that yields the capacitance of a lead. Once the capacitance of an individual lead has been measured, the microcontroller 200 may direct the multiplexer to address another pin corresponding to a lead on the acousto-electrical probe and repeat the steps described above for each lead under test. The capacitance of each of the leads may then be communicated to the operator via an external device, such as an LCD or PC.

Other circuitry may also be interfaced to the microcontroller 200. For example, an 8 MHz clock oscillator 208 may be connected to the EXTAL pin of the microcontroller 200 through a resistor R2 (e.g., 10Ω) to generate clock pulses required for the operation of the microcontroller 200. Additionally, a three pin connector 204 may be connected to the MODB/VSTBY pin of the microcontroller 200. The connector 204 permits the microcontroller 200 to be placed into run mode and programming mode by modifying the position of a jumper 205. As stated above, the microcontroller 200 may also be interfaced with an LCD through an LCD connector 234. The LCD may be operable to display information about the leads of an acousto-electrical probe that may be helpful to the operator. To control the operation of the LCD, the microcontroller 200 may use the PB0-PB7 and PD2-PD4 pins. A potentiometer 230 (e.g., 10 kΩ) may also be coupled to the LCD connector 234 to allow the operator to adjust the contrast of the LCD. Additionally, a heartbeat LED 226 may be coupled to the microcontroller 200 to provide status information to the operator. Such status information may include operational modes, error codes, or the like. Moreover, the RESET pin on the microcontroller 200 may also be interfaced to external reset circuitry to provide the RTT 250 with reset capabilities. For example, a reset switch 212, a diode 222, a resistor R3 (e.g., 47.5 kΩ), and a capacitor C16 (e.g., 1 uF) may be used to provide reset circuitry for the microcontroller 200.

Figure 8:
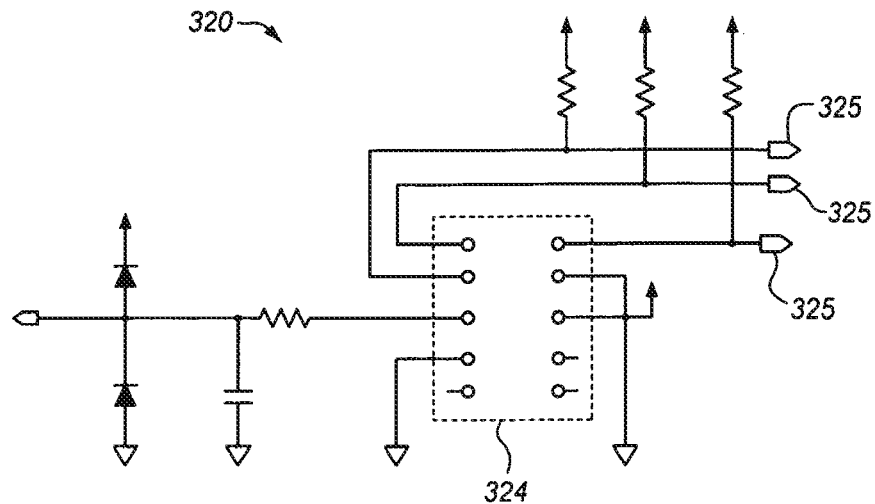
FIG. 8 is a circuit schematic of a mode select switch module of the exemplary retermination test tool.

Additionally, the RTT 250 may be configured with a mode select switch 324, as illustrated with the mode select switch module 320 of FIG. 8. For example, when a user wishes to implement one of the scans, such as the Ground Scan, the user may input such a request via a user interface (e.g., a button that connects a switch or a software interface that initiates the Ground Scan mode). In this regard, the mode select switch 324 may receive the input via the mode switch inputs such that the mode select switch 324 properly addresses the test probe as described hereinabove.

As discussed above, the RTT 250 may also be configured to include an external device, such as a PC. The transmit/receive pins (i.e., RXD and TXD) of the microcontroller 200 may be connected to a serial driver/receiver 218. The serial driver/receiver 218, in this embodiment, is an RS-232 integrated circuit (e.g., a MAX232 produced by Maxim Integrated Products, Inc.) that is used to drive serial transmit/receive signals between the microcontroller 200 and a PC. The serial driver/receiver 218, in this embodiment, may be connected to an RS-232 connector 214. This configuration allows the microcontroller 200 to communicate to a PC via a serial communication link. In this embodiment, the previously described operational modes of the RTT 250 may be used in conjunction with a custom software program running on the PC to provide a user-friendly interface for testing and repairing acousto-electrical probes. For example, the program may display a diagram of the PCB of the acousto-electrical probe under test including all of its solder pads. When the operator touches a lead of the acousto-electrical probe to the test probe of the RTT 250, the program may visually indicate which solder pad on the PCB the lead should be terminated. Alternatively or additionally, the program may visually or audibly alert the operator when a particular lead is in contact with the test probe of the RTT 250. The operator may then connect another lead to the test probe and continue in this fashion until all the leads have been properly terminated. The program may also be configured to visually or audibly report which leads are grounded or open. For example, the operator may input a command to the PC that causes the PC to display a listing of all the leads that are grounded. The program may also be configured to display the capacitance of one or more leads in response to a command from the operator. The capacitance may be displayed numerically, in chart form, or any other suitable form. The program may also be configured to test numerous types of acousto-electrical probes. For example, the program may provide a menu where the operator may select a specific acousto-electrical probe from a list. If acousto-electrical probes that are desired to be tested are not included in the menu, the program may also permit the operator to input characteristics (e.g., number of leads, PCB diagrams, etc.) of the acousto-electrical probes so that they may be tested. Furthermore, the program may be configured to automatically detect the type of acousto-electrical probe connected to the RTT 250 based on one or more characteristics of the probe by using one or more of the previously described operational modes.

Although shown and described as a circuit that is configured to communicate with a PC or other device via the RS-232 connector 214, the invention is not intended to be so limited. For example, other communication schemes (e.g., parallel communications, serial Ethernet communications, IEEE 1394 communications, etc.) could be configured with the RTT 250 to convey data. Additionally, the RTT 250 may be configured as a card that operates within the constructs of the PC's operating system.

Figure 9:
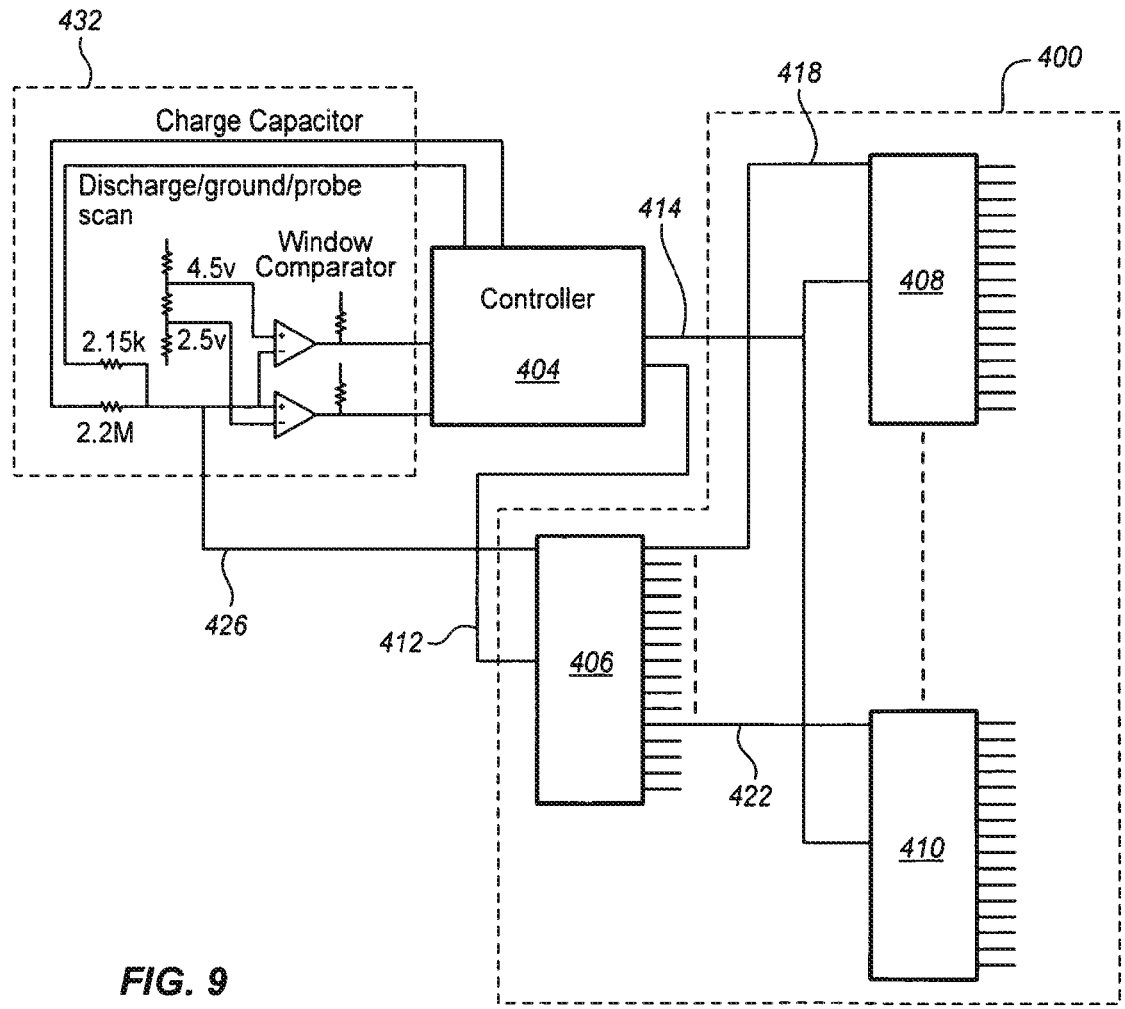
FIG. 9 is a circuit schematic that illustrates a multiplexing portion of an exemplary retermination test tool.

FIG. 9 is a circuit schematic that illustrates an exemplary multiplexing system 400 and various control circuitry that may be used in an RTT, such as the multiplexer 108 of the RTT 100 of FIG. 4. More specifically, FIG. 9 illustrates an implementation of a 1:192 channel multiplexing system using thirteen 1:16 channel multiplexers. In this embodiment, a controller 404 (e.g., the controller 200 shown in FIG. 5) may communicate with electrical sensing circuitry 432 and thirteen 1:16 channel multiplexers (e.g., the multiplexers 406, 408, 410) to test transducer leads of an acoustic electrical probe that is communicatively coupled via the multiplexing system 400. The multiplexers may be any type of 16 channel analog multiplexer/demultiplexer such as the CD4067 multiplexer manufactured by Texas Instruments. Each multiplexer is shown to have 16 input channels (i.e. CH0-CH15), an output channel (i.e. COM), and four control lines (i.e. S0-S3). The multiplexer 406, in this embodiment, serves as a master multiplexer. Although only two are shown for simplicity, twelve slave multiplexers (e.g. the slave multiplexer 408, the slave multiplexer 410) may be electrically coupled to the master multiplexer 406. The multiplexing system 400 may be configured to allow the controller 404 to direct the multiplexing system to select an individual lead on an acousto-electrical probe using the output control signals MUX_D0-MUX_D7. The input channels of each of the twelve slave multiplexers may be electrically coupled to connector pins that are connected to individual leads of the acousto-electrical probe. The output of each slave multiplexer (e.g., the slave multiplexers 408 and 410) may be electrically coupled to an input channel of the master multiplexer 406. The output of master multiplexer 406 may be electrically coupled to a test node 426, which may be used by the electrical sensing circuitry 432 to determine one or more electrical characteristics of an individual lead of the acousto-electrical probe. The MUX_D0-MUX_D3 lines of the controller 404 may be coupled to the four control lines S0-S3 of each slave multiplexer. Similarly, the MUX_D4-MUX_D7 lines of the controller 404 may be coupled to the four control lines S0-S3 of the master multiplexer 406. In this configuration, the controller 404 may use the MUX_D4-MUX_D7 control lines to address a particular slave multiplexer, and the MUX_D0-MUX_D3 control lines to address a specific pin on a slave multiplexer. Therefore, the controller 404 can effectively implement a 1:192 multiplexer to test an acousto-electrical probe having up to 192 leads using readily available 1:16 channel analog multiplexers. Once an individual lead is selected and therefore electrically coupled to the test node 426, the electrical sensing circuitry 432 may function in accordance with the various operational modes discussed above to sense one or more electrical characteristics of the lead under test. However, the invention is not intended to be so limited. The embodiment herein is merely shown with a 1:192 multiplexer because acousto-electrical devices are generally configured with a maximum of 192 leads. If such a device were to use more leads (e.g., to improve resolution), the multiplexer could be adapted to meet the requirements of the device. For example, should an acousto-electrical probe be configured with more than 192 transducers, and thus more than 192 transducer leads, the multiplexing system 400 may be configured with more master/slave multiplexers to accommodate the increased number of connections. Accordingly, the embodiment shown herein is merely intended to show one example of an adaptable acousto-electrical probe testing tool.

Figure 10:
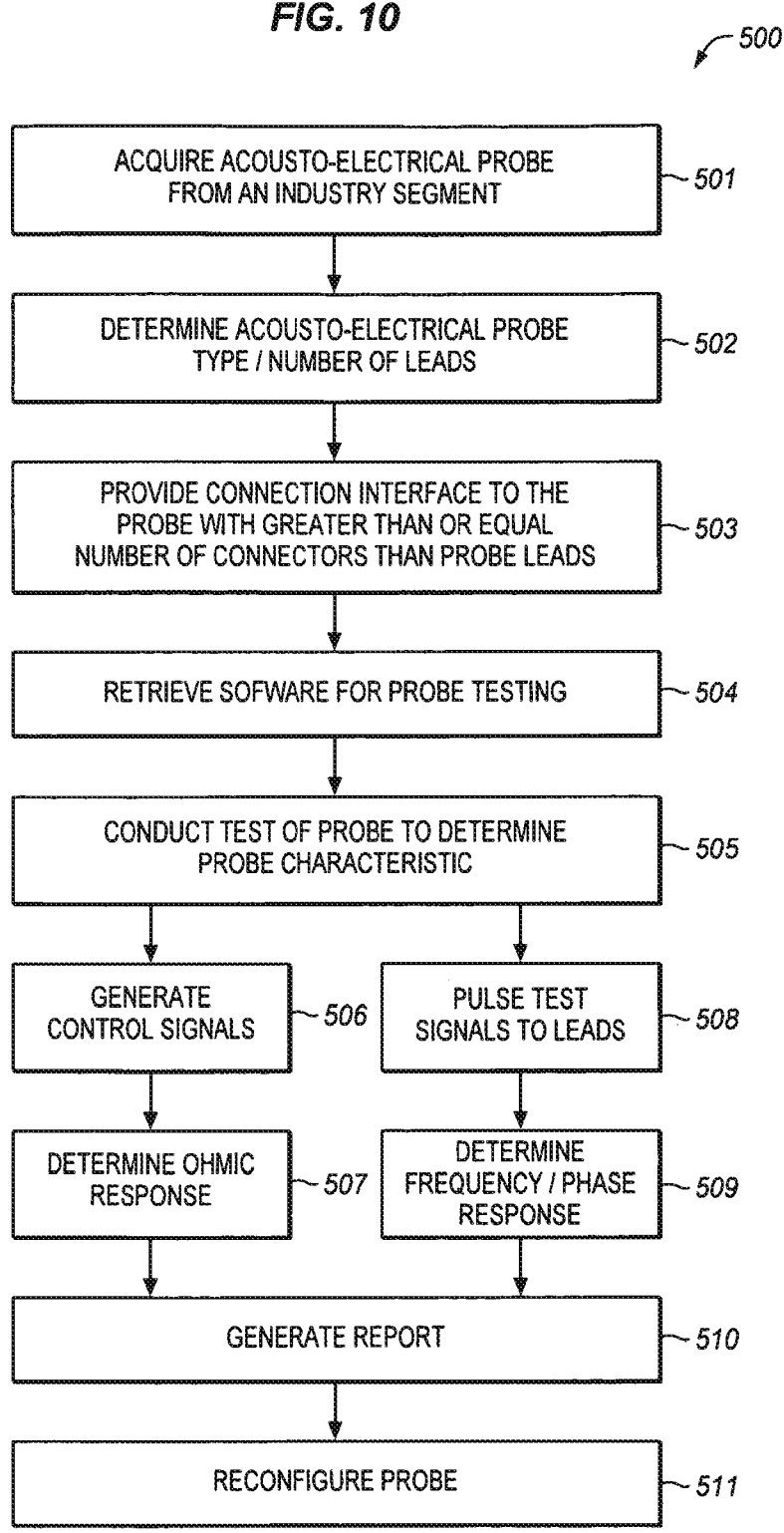
FIG. 10 is a flowchart of a process for reconfiguring an acousto-electrical probe.

FIG. 10 is a flowchart of a process 500 for reconfiguring an acousto-electrical probe, such as ultrasound probe. For example, as described hereinabove, ultrasound probes may find themselves in a state of disrepair due to misuse, neglect, and even general handling. In such cases, an ultrasound probe often has components that are still operable, such as the transducers configured at the probe/human interface. It is often the case that the transducer leads themselves are the components that are no longer operable (e.g., broken and/or detached from the transducers). All too often, a medical industry segment (e.g., a hospital with, a doctor's office, and original equipment manufacturer, a retailer, etc.) employing such a device would simply replace the ultrasound probe at a relatively substantial cost. In this regard, the process 500 provides a means for returning an acousto-electrical probe to an operational status ready for reintroduction to the medical industry segment.

The process 500 may initiate when the acousto-electrical probe is acquired from the medical industry segment, in the process element 501. For example, once the acousto-electrical probe has been deemed inoperable or at least not in compliance with a particular standard, the medical industry segment (e.g., a doctor's office, hospital, or the like) may request replacement of the acousto-electrical probe. In this regard, a configuration facility may acquire the acousto-electrical probe of the medical industry segment and provide the medical industry segment with a temporary acousto-electrical probe (e.g., a loaner probe) or even a permanent replacement probe (e.g., a reconfigured probe).

Once acquired, a determination may be made as to the type of acousto-electrical probe (e.g., brand, model, etc.), in the process element 502. In this regard, a determination may be made as to the number of transducer leads of the acousto-electrical probe. In response thereto or as a part of the determination process, a connection may be provided to the probe in the process element 503. For example, a universal connection interface may be configured with a number of connectors that is greater than or equal to the number of leads of an ultrasound probe. This universal connection interface may be coupled to a processor which interrogates connectors of the connection interface to determine the number of transducer leads connected via the associated probe connection interface. Alternatively, a connection interface may be configured such that number of connectors therewith matches the number of connectors of a probe connection interface. A device employing such a connection interface may be adaptable based on the "switchability" of the connection interfaces. For example, multiple connection interfaces may be configured with a particular test device wherein each connection interface is configured for connecting to a particular probe connection interface. Alternatively, the test device may be configured with a communications interface that allows for a connection interface to be readily swapped out with other connection interfaces, wherein each connection interface is configured for particular probe connection interface.

In any case, once a determination is made as the type of probe and/or the number of probe leads, software may be retrieved to perform probe testing, in the process element 504. The software modules may be device specific and/or configured to perform a particular test. For example, a test device may include a plurality of software modules wherein at least some number of the software modules is configured according to ultrasound probe type. The software modules may call other more generic software modules that are used to implement testing of a particular ultrasound probe that is connected via the connection interface. The testing may reveal certain probe characteristics, in the process element 505, once implemented.

In one embodiment, a processor, as directed by the software modules, generates control signals that are applied to ultrasound transducer leads via the connection interface, in the process element 506. The processor may determine an ohmic response (e.g., conductivity of the leads), in the process element 507, to determine whether the transducer leads have been broken, detached, and/or shorted. For example, based on a resistance value, the processor may determine which transducer leads are malfunctioning. Alternatively or additionally, the processor may be configured to generate control signals that test the transducers of the ultrasound probe, in the process element 508. For example, the processor may pulse test signals to the leads via the connection interface such that the transducers radiate an acoustic pulse. In this regard, the transducers may receive reflections of the acoustic pulse which are thereby converted into electronic signals. The processor may determine a frequency and/or phase response of such received signals, in the process element 509, as described hereinabove.

Regardless of the test, the process 500 may formulate a report regarding the operability of the acousto-electrical probe, in the process element 510. For example, once certain transducer leads of an ultrasound probe had been deemed malfunctioning, a display interface may display a map of the probe connection interface that further identifies those transducer leads which are malfunctioning. Such a display may be performed in a variety of ways, many of which are described hereinabove. With the malfunctioning leads identified, the acousto-electrical probe may be reconfigured, in the process element 511 by, for example, reattaching and/or replacing transducer leads. Similarly, malfunctioning transducers may be determined from frequency response displays such that individual transducers may be repaired or the transducer "head" may be replaced.

Once the acousto-electrical probe is reconfigured, the acousto-electrical probe may be reintroduced to the medical industry segment. For example, a doctor's office with a loaner ultrasound probe may return the loaner probe in exchange for the repaired ultrasound probe. Alternatively, the doctor's office may purchase a reconfigured ultrasound probe at a cost that may be substantially less than a new ultrasound probe.

Figure 11:
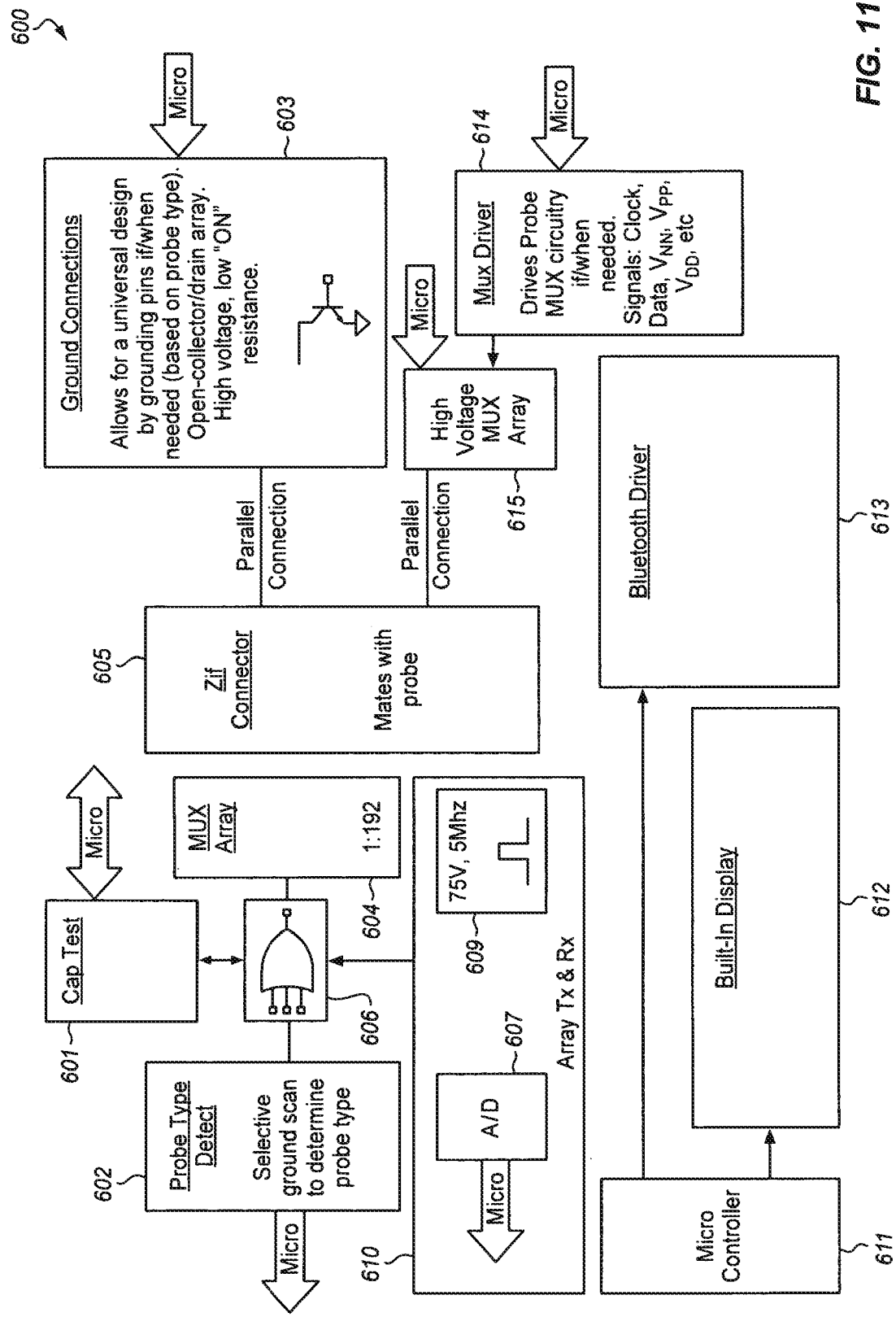
FIG. 11 is a block diagram of an exemplary transducer characterization module.

FIG. 11 is a block diagram of an exemplary ultrasound probe characterization module 600. In this embodiment, the transducer characterization module 600 may include certain features described hereinabove, such as the Capacitance Scan Mode (e.g., capacitance test module 601) and the Ground Scan Mode (e.g., the probe type detection module 602), as well as other features that may be used to characterize transducers of an ultrasound probe. For example, the capacitance test module 601 may be used to test the capacitance of the electrical lead of a transducer that is connected to the zero insertion force connector 605. Such a test may include initially discharging capacitance in a lead followed by charging the capacitance of the lead until a certain voltage level has been attained, such as the 2.5 V described hereinabove. During this charging of the capacitance, the microcontroller 611 may count such that a duration may be computed and a capacitance of the lead be determined therefrom. The capacitance test module 601 may perform the capacitance test for each lead connected to the zero insertion force connector 605.

The probe type detection module 602 may use the Ground Scan Mode to determine the type of ultrasound probe coupled to the zero insertion force connector 605. For example, ultrasound probes are offered by a variety of manufacturers. These probes may, therefore, have varying configurations including a varying number of transducer leads. The zero insertion force connector 605, in this regard, may be configured to "mate" with a variety of ultrasound transducer probe types. Thus, any ultrasound coupled to the zero insertion force connector 605 may require an additional identification. The probe type detection module 602 may perform a ground scan as described hereinabove to determine a number and configuration of transducer leads coupled to the zero insertion force connector 605. In this regard, the probe type detection module 602 may be communicatively coupled to the microcontroller 611 where software modules, also described hereinabove, may be called by the microcontroller 611 to determine the type of ultrasound probe connected to the zero insertion force connector.

Differing somewhat from the embodiments described hereinabove is the transmit/receive module 610, which is used to determine the operational characteristics of the transducers configured within an ultrasound probe. For example, the transmit/receive module 610 may include a pulse generator 609 that generates and transmits pulses that are used to stimulate individual transducers configured within an ultrasound probe. In one embodiment, the pulse generator 609 is configured to provide approximately 75 V pulses at a pulse repetition frequency of 5 MHz. In response to transmitting the pulses, the transmit/receive module 610 may receive the pulses as they are reflected from a target. The received reflected pulses may be digitized by the analog to digital converter 607 such that they may be processed by the microcontroller 611. In this regard, the microcontroller 611 may determine the frequency and/or phase characteristics of individual transducers. In particular, the ultrasound probe characterization module 600 may include software that is used by the microcontroller 611 to observe ultrasound characteristics much like an ultrasound medical device would.

Also configured with the ultrasound probe characterization module 600 is a universal ground connection module 603. The universal ground connection module 603 provides ground connections to selected transducer leads. For example, when a technician is characterizing an ultrasound probe, the technician may require ground connections to one or more of the transducer leads within the ultrasound probe. The universal ground connection module 603 may provide a simultaneous connection to ground for selected transducer leads (e.g., regardless of the ultrasound probe type) as opposed to scanning the individual transducer leads employed by the Ground Scan Mode. In one embodiment, the universal ground connection module 603 includes an open collector/drain array that provides relatively high-voltage and low resistance when "turned on".

Additionally, the ultrasound probe characterization module 600 may include a multiplexer (MUX) driver module 614 that is used to drive individual transducers of the probe when desired. For example, the MUX driver module 614 may be coupled to a MUX array 615 which in turn couples the MUX driver module 614 to individual transducer leads of an ultrasound probe coupled to the zero insertion force connector 605. Instead of merely applying a voltage, the MUX driver module 614 may transmit a plurality of signal types including data signals, clock signals, voltages, variable voltage waveforms, etc. These signals may be used to selectively test the transducer leads and/or the transducers of an ultrasound probe. For example, a technician may wish to determine the data transfer characteristics of a particular transducer lead. In this regard, the technician may transmit a data signal to the selected transducer lead. Other leads, which are not necessarily transducer leads, within the ultrasound probe may be similarly tested. In another example, the technician may transfer a clock signal through ultrasound probe lead to determine possible data transfer rates for the lead.

The ultrasound probe characterization module 600 may also include a display 612 that is communicatively coupled to the microcontroller 611 to display information to a technician. For example, the ultrasound probe characterization module 600 may be configured as a portable tool that may be used by a technician in the field. A built-in display 612 may provide the technician with valuable information (e.g., capacitance test information of transducer leads, broken lead identification, acoustic/electrical characteristics of an ultrasound probe, the number of transducers that are operational, etc.) when attempting to repair or at least diagnose an inoperable ultrasound probe. In this regard, the microcontroller 611 may process information from a particular test (e.g., from the capacitance test module 601, the prototype detection module 602, etc.) and display the results of that test with the built-in display 612 for observation by the technician.

Alternatively or additionally, the ultrasound probe characterization module 600 may include a Bluetooth driver 613 which may be used to communicate information regarding a particular test to a device maintained by the technician. For example, test information may be wirelessly transferred from the ultrasound probe characterization module 600 to a handheld device (e.g., a cell phone, a PDA, a smart phone, a laptop computer, etc.) for observance and/or additional processing. While a Bluetooth driver 613 may be particularly useful for wirelessly transmitting information from one device to another, the invention is not intended to be limited to such a wireless transfer. For example, other wireless communication means may be employed as well as wired communication means (e.g., serial communications or parallel to medications).

Also shown in this embodiment is the test selection module 606. The test selection module 606 may be implemented in a variety of ways. In this embodiment, the test selection module 606 is implemented as a logical OR gate to select which tests may be performed on an ultrasound probe connected to the zero insertion force connector 605. For example, a technician using the ultrasound probe characterization module 600 may select a test through the built-in display or other means, such as a button. The microcontroller 611 may transfer a selection signal to the test selection module 606 such that a desired test is selected.

Figure 12:
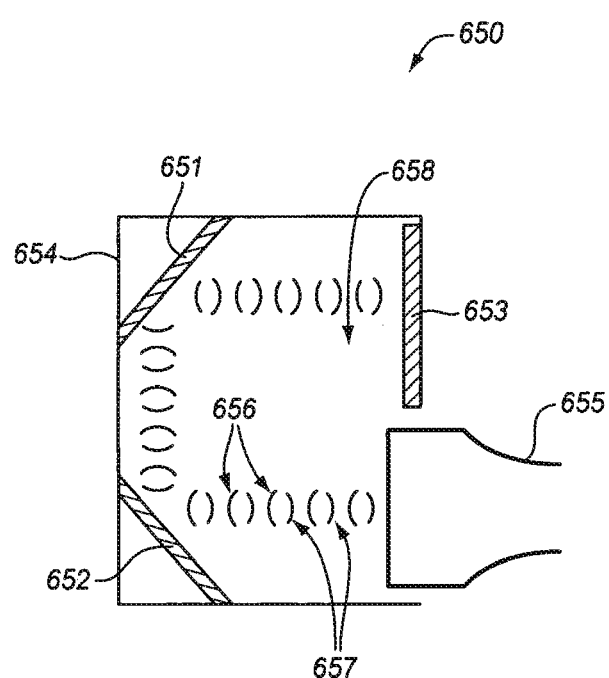
FIG. 12 is an illustration of an exemplary reflection module.

FIG. 12 is an illustration of an exemplary reflection module 650. In this embodiment, the reflection module 650 may be configured for attaching to an ultrasound probe 655 such that acoustic signals may be transmitted from and reflected to the ultrasound probe 655 during testing. For example, the reflection module 650 may include a housing 654 that includes reflective elements 652, 651, and 653 that reflects acoustic signals 656 from the ultrasound probe 655 along a particular path. As the acoustic signals 656 impinge the reflective element 653, the reflected signals 657 are propagated back along the same path to the ultrasound probe 655 such that the signals may be received by the transducers of the ultrasound probe and subsequently processed by an ultrasound characterization module, such as that shown in FIG. 11.

The reflection module 650 may include a transmissive medium 658 that is used to propagate the acoustic signals (e.g., acoustic signals 656 and 657). The transmissive medium 658 may be configured in a variety of ways that alleviate the need for testing the ultrasound probe 655 in a "bath". For example, ultrasound probe testing often required use of a water bath in some sort of container to propagate acoustic signals from an ultrasound probe through the water bath for reflection back to the ultrasound probe, where the acoustic signals would be received by the transducers of the probe and processed by the ultrasound test equipment. This bath requirement often makes testing in the field impractical or, in some cases, impossible. Thus, testing of an ultrasound probe previously needed to be transferred to a test facility where proper testing could be performed (i.e., using a water bath or another type of liquid bath). The reflection module 650 overcomes such obstacles by providing a transmissive medium 658 in a self-contained housing 654. While the transmissive medium 658 may be configured in a variety of ways, one exemplary media may include silicone. However, since the reflection module 650 includes the self-contained housing 654 other mediums may be used, such as gels, foams, room temperature vulcanized material, or any other elastic material capable of propagating acoustic waves.

Additionally, the illustrated reflection module 650 is not intended to limit the invention to a particular number of reflection elements. Rather, the reflection module 650 illustrates one exemplary manner which provides a means for forming a propagation path of a certain length, such as that distance used in an ultrasound probe bath. Other lengths or configurations of propagation may be implemented as a matter of design choice. For example, a reflection module may be configured with a single reflective element that directly receives acoustic waves from the ultrasound probe and directly reflects the waves to the ultrasound probe.

While the invention has been illustrated and described in detail in the drawings and foregoing description, such illustration and description is to be considered as exemplary and not restrictive in character. For example, certain embodiments described hereinabove may be combinable with other described embodiments and/or arranged in other ways (e.g., process elements may be performed in other sequences). Additionally, the embodiments shown and described herein may provide certain advantages in quickly diagnosing and repairing ultrasound probes of the medical industry. However, the invention is not intended to be limited to the medical device industry. Rather, the embodiments above may provide a means for addressing a variety of acoustic devices that use transducers. Accordingly, it should be understood that only the preferred embodiment and variants thereof have been shown and described and that all changes and modifications that come within the spirit of the invention are desired to be protected.

The invention claimed is:

1. An acousto-electrical probe testing apparatus comprising:
   a connection interface to connect to a plurality of acousto-electrical probes of different probe types having different numbers of transducer leads, the connection interface to be configured to accommodate a selected acousto-electrical probe based on connection type information identified for a probe type associated with the selected acousto-electrical probe; and
   a processor to identify the probe type of a first acousto-electrical probe when the first acousto-electrical probe is coupled to the connection interface based on a selected operational mode and an interrogation of connectors in the connection interface to determine a number of leads coupled to the connection interface, the selected operational mode including at least one of a ground scan mode, a probe scan mode, or a capacitance scan mode, the processor to:
   trigger a test of the first acousto-electrical probe based on the probe type and the selected operational mode, the test including generation of a control signal to be applied to the leads of the first acousto-electrical probe coupled to the connection interface; and
   process a plurality of responses to the control signal from the leads of the first acousto-electrical probe to determine when a lead is at least one of broken or detached from the first acousto-electrical probe.

2. The apparatus of claim 1, wherein the first acousto-electrical probe includes an ultrasound probe.

3. The apparatus of claim 1, wherein the control signal includes a control signal generated to determine an ohmic response related to conductivity of the leads.

4. The apparatus of claim 1, wherein the control signal includes a pulse test signal to be sent to the leads to produce an acoustic pulse radiating from the leads.

5. The apparatus of claim 4, wherein the processor is to convert received reflections of the acoustic pulse into an electronic signal.

6. The apparatus of claim 5, wherein the processor is to determine at least one of a frequency or phase response of the electronic signal to determine when a lead is at least one of broken or detached from the first acousto-electrical probe.

7. The apparatus of claim 1, wherein the interrogation of connectors in the connection interface by the processor includes generating a second control signal to determine a configuration of the first acousto-electrical probe coupled to the connection interface.

8. The apparatus of claim 1, wherein the processor is to multiplex a plurality of control signals based on the probe type.

9. The apparatus of claim 1, further including a test probe to be contacted by a lead of the first acousto-electric probe to apply the control signal to the leads of the first acousto-electrical probe.

10. The apparatus of claim 1, wherein the selected operational mode is to be selected from a plurality of operational modes based on configuration of the apparatus.

11. The apparatus of claim 1, further including a counter to increment during the test of the first acousto-electrical probe.

12. The apparatus of claim 1, wherein the apparatus further includes:

a memory including software to be executed by the processor to execute the test; and a library of known probe types to configure the test and the connection interface.

13. The apparatus of claim 1, further including a multiplexer to drive individual transducers of the first acousto-electrical probe.

14. The apparatus of claim 1, further including a display interface to output information when a lead is at least one of broken or detached from the first acousto-electrical probe.

15. The apparatus of claim 1, wherein the connection interface is to enable the processor to test at least a single lead of the first acousto-electrical probe.

16. The apparatus of claim 15, wherein the single lead is to be selected by the processor using a multiplexer.

17. The apparatus of claim 1, further including a comparator to compare a response to the control signal with a reference signal.

* * * * *